United States Patent [19]

Brotz

[11] Patent Number: 5,213,338
[45] Date of Patent: May 25, 1993

[54] BRAIN WAVE-DIRECTED AMUSEMENT DEVICE

[76] Inventor: Gregory R. Brotz, P.O. Box 1322, Sheboygan, Wis. 53081

[21] Appl. No.: 767,853

[22] Filed: Sep. 30, 1991

[51] Int. Cl.$^5$ ............................ A63F 9/00; A61B 5/04
[52] U.S. Cl. ................................... 273/460; 273/453; 273/454; 434/237; 128/731
[58] Field of Search .................... 84/600, 464 R, 465, 84/468; 128/731, 734, 746; 340/700, 701; 273/85 G, 440, 454, 460, 445, 453, 161; 437/237

[56] References Cited

U.S. PATENT DOCUMENTS

| | | | |
|---|---|---|---|
| 4,358,118 | 11/1982 | Plapp | 273/454 |
| 4,926,969 | 5/1990 | Wright et al. | 128/731 |
| 4,949,726 | 8/1990 | Hartzell et al. | 128/731 |
| 4,955,388 | 9/1990 | Silberstein | 128/731 |

Primary Examiner—A. Jonathan Wysocki
Assistant Examiner—Helen Kim
Attorney, Agent, or Firm—William Nitkin

[57] ABSTRACT

A game having circuitry for the conversion of a player's brain wave intensity to direct the movement of a rotating circular visual display. The game in one embodiment can be played by two players competing with one another and the visual display can include a variety of changing patterns.

6 Claims, 9 Drawing Sheets

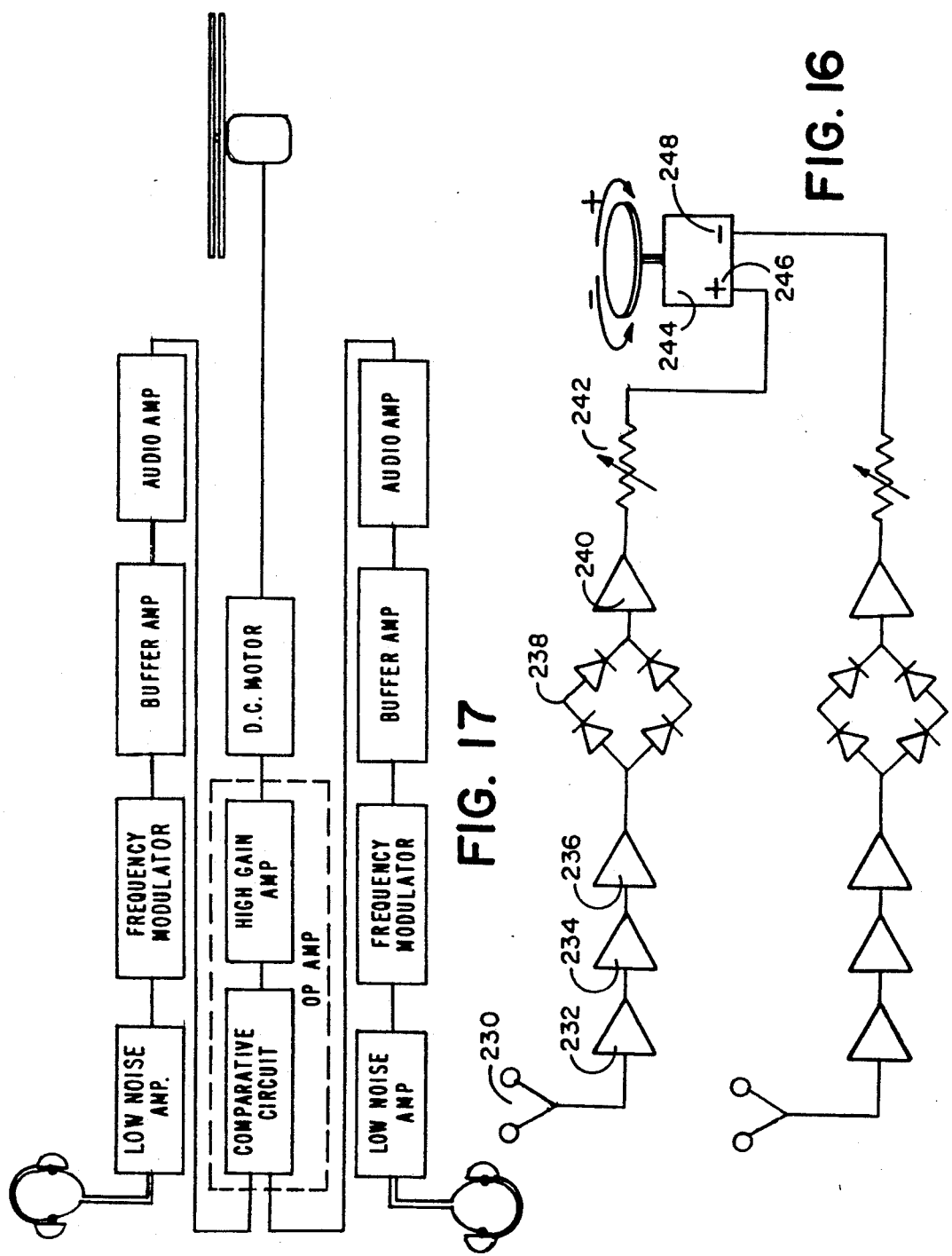

BRAIN WAVE-DIRECTED AMUSEMENT DEVICE

BACKGROUND OF THE INVENTION

1. Field of the Invention

The present invention relates to an amusement device controlled by the user's brain waves and more particularly relates to an amusement device that displays various light patterns controlled by the brain wave production of one or more players.

2. Description of the Prior Art

It has been long known that brain waves can be recorded, and signals thereof used, to control a variety of electronic visual display patterns depending upon the amount of particular kinds of brain waves detected emanating from an individual. Such visual display systems are exemplified by the Brady patents, U.S. Pat. Nos. 4,056,805 and 4,140,997. These patents disclose systems including detecting brain waves and producing various colored displays that operate as a function of the particular brain waves detected from the subject. An entertainment device utilizing brain waves has also been developed by Miguel Hidalgo-Briceno as disclosed in U.S. Pat. No. 3,855,998 which shows an entertainment device including sensing means to detect theta waves from the brain. Depending upon the state of the subject who is observing various audio-visual stimulation, the device controls flashing colored lights and other visual images and stimulations to help the subject alter his brain waves to achieve a state of aesthetic experience.

SUMMARY OF THE INVENTION

It is an object of this invention to provide a brain wave-controlled amusement device which operates based on the brain wave patterns detected from one or more players. The device can produce a plurality of visual patterns and light arrangements on a display unit depending upon the player's brain wave output. The device of this invention can be used for relaxation, amusement or as a competitive game with other players. A cap which has electrode elements therein is applied to each user's head which electrodes by contact with the head in well-known prior art methods receive alpha, beta, delta and/or theta waves which waves can be monitored individually for each player by a brain wave monitor, also well known in the prior art, included in the cap or in the base of the device. The brain wave monitor measures the intensity of waves produced and then forwards a signal representing this intensity to a proportional controller which in turn controls the amount of current being sent to a series of electromagnets on the display unit portion of the device. In one embodiment the electromagnets are arrayed around and under the outer edges of a rotatable round top plate. The top plate also can contain magnets in its outer edges which are attracted or repelled by the electromagnets in a way as described below to cause the top plate to rotate. The top plate can be rotatably mounted on a pin bearing on the top of the device of this invention, and the electromagnetic force of the electromagnets controlled by the proportional controller propels the permanent magnets to rotate the top plate. There may be sets of magnets, for example, one, two, three or more on each side of the rotatable top plate assigned to each player. In one embodiment the top plate can include a substantially transparent sheet which has a fringe pattern imprinted or displayed thereon with a second fringe pattern on a lower surface of the unit under the top plate. When these patterns are viewed through the rotating top plate, a moire pattern can be observed. The second pattern can also be produced from an array of a plurality of LEDs or a liquid crystal display polarizing sheet producing varying kinds of patterns. The liquid crystal pattern display can be controlled by a pattern memory unit, the pattern selection of which is controllable by the players to produce a variety of effects under the rotating top plate, and the rotation speed of which is controlled by the proportional controller which in turn is controlled by the output of the brain wave monitor. Thus the pattern is controlled both by the amount of brain waves that are produced by each player and by the configuration of the first and second patterns selected. When a single player is using this device, the moire pattern changes in relation to the amount of brain wave production and resulting patterns of a soothing nature can be produced to help reinforce relaxation behavior as in biofeedback devices. The pattern created by the LED array or liquid crystal display can also be made to move and/or rotate by the memory unit, and it can rotate, for example, at the same speed that the top plate rotates. In some instances a player can try to produce a sufficient intensity of brain waves to cause the rotation of the top plate to keep up with the rotation of the pattern on the LED array or liquid crystal display therebelow. The production of brain waves can be influenced by viewing the moire patterns and such viewing can create a state of relaxation for a player. When the device is used by multiple players, each player will control his own series of electromagnets disposed under the edges of the rotating top plate. These electromagnets will produce changes in speed and direction of the rotating top plate so that it rotates at a controlled speed either clockwise or counterclockwise. For example, one player may produce brain waves in an amount that will cause the top plate to rotate counterclockwise while the other player produces waves to cause the top plate to move clockwise with the force of each magnetic series cancelling each other out. If the players are equal in brain wave production, the top plate will be stationary. If one of the players produces more waves than the other, the magnets or magnetically attractive material on the top plate will slowly start the top plate rotating in the direction controlled by that player. A rotation counter can be included within the device. Also a motion sensor fixed below the rotating top plate can sense the movement of a magnetic circular strip contained in the top plate which information is directed to a computer contained within the device. The device can calculate the total amount of speed changes for each player and determine which player is the winner of the game depending upon the total amount of brain waves produced.

The rotating top plate can also be made of an optical grating which can produce an interference pattern combined with the image on the lower plate to produce interesting optical effects. The device can also be utilized as a sole electronic display that changes according to the alpha, beta, delta or theta waves produced or in a combination of two or a combination of two or more frequencies. Colored lights or LEDs can be used to make displays of various colors or to change the color of the display in relation to the alpha or beta waves produced and such display could pulsate in a number of ways to distract or reward the user. There also can be a button which when pushed, reverses the polarity of the electromagnets thus changing the display. One can, of course, as in the prior art, listen to music during playing the game which will help influence the brain wave production and the type or frequency of the brain waves. One feature of this invention can be that each player can have a "zapper" button that can be pressed once during a preselected period of time that will turn the viewing screen blank so as to counter the brain wave production of an opponent and gain advantage during the game. The use of a zapper button will create an element of surprise and will cause an opponent to lose a certain brain wave state that such opposing player may have attained. Such a zapper button could be used once every 4-5 minutes during play. The patterns chosen in the game can also be related to music or musical passages or even computer-generated music which the speaker could broadcast to the players and it could be fully rhythmic, semi-rhythmic or merely random notes that may be tuned with other notes being generated for the production of such music during playing of the game.

BRIEF DESCRIPTION OF THE DRAWINGS

FIG. 16 illustrates a schematic diagram of circuitry to operate a reversible DC motor for the rotation of the top plate.

FIG. 17 illustrates a block diagram of circuitry for operation of a reversible DC motor for rotation of the top plate.

DESCRIPTION OF THE PREFERRED EMBODIMENT(S)

Figure 1:
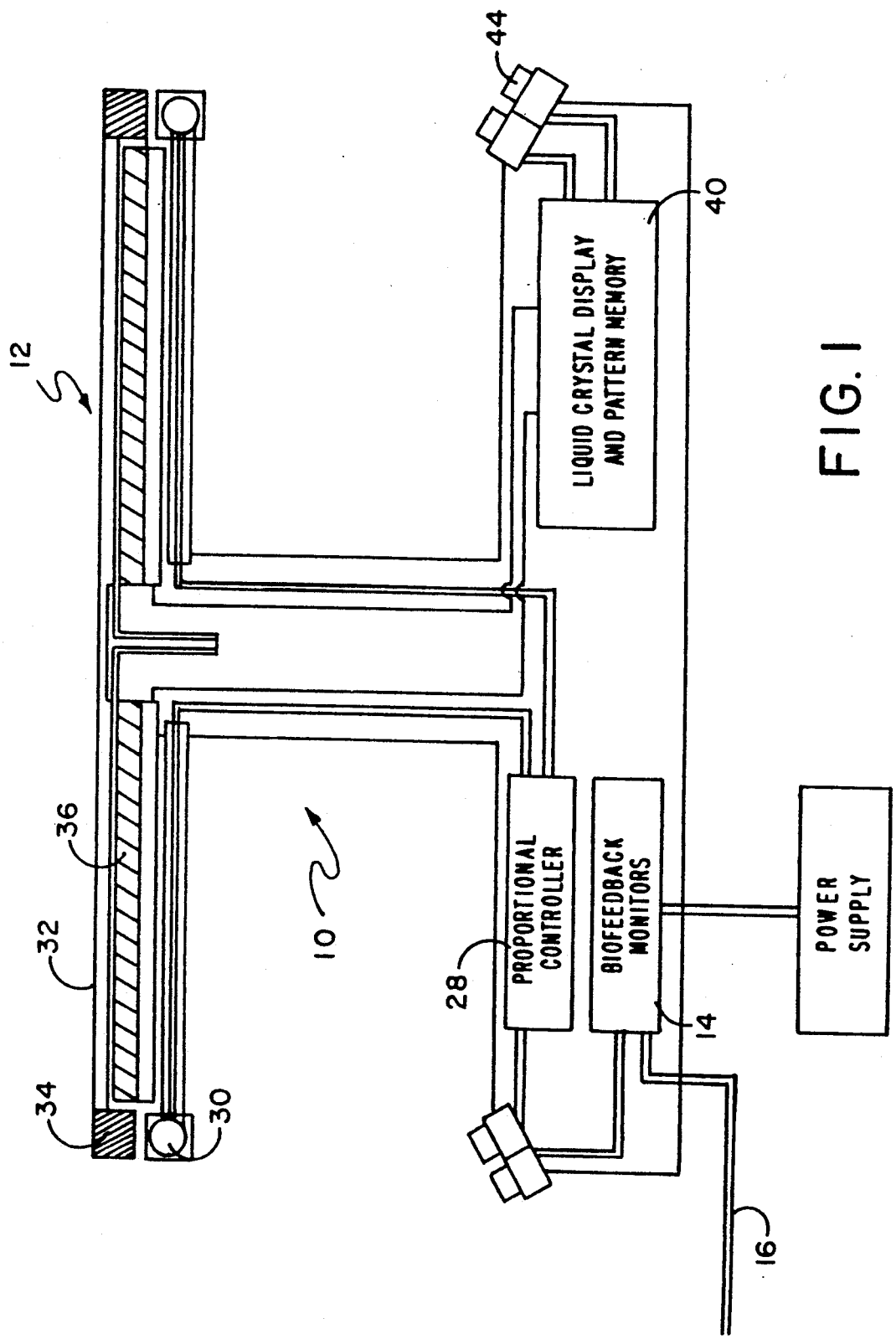
FIG. 1 illustrates a cross-sectional view through an embodiment of the device of this invention.
Figure 2:
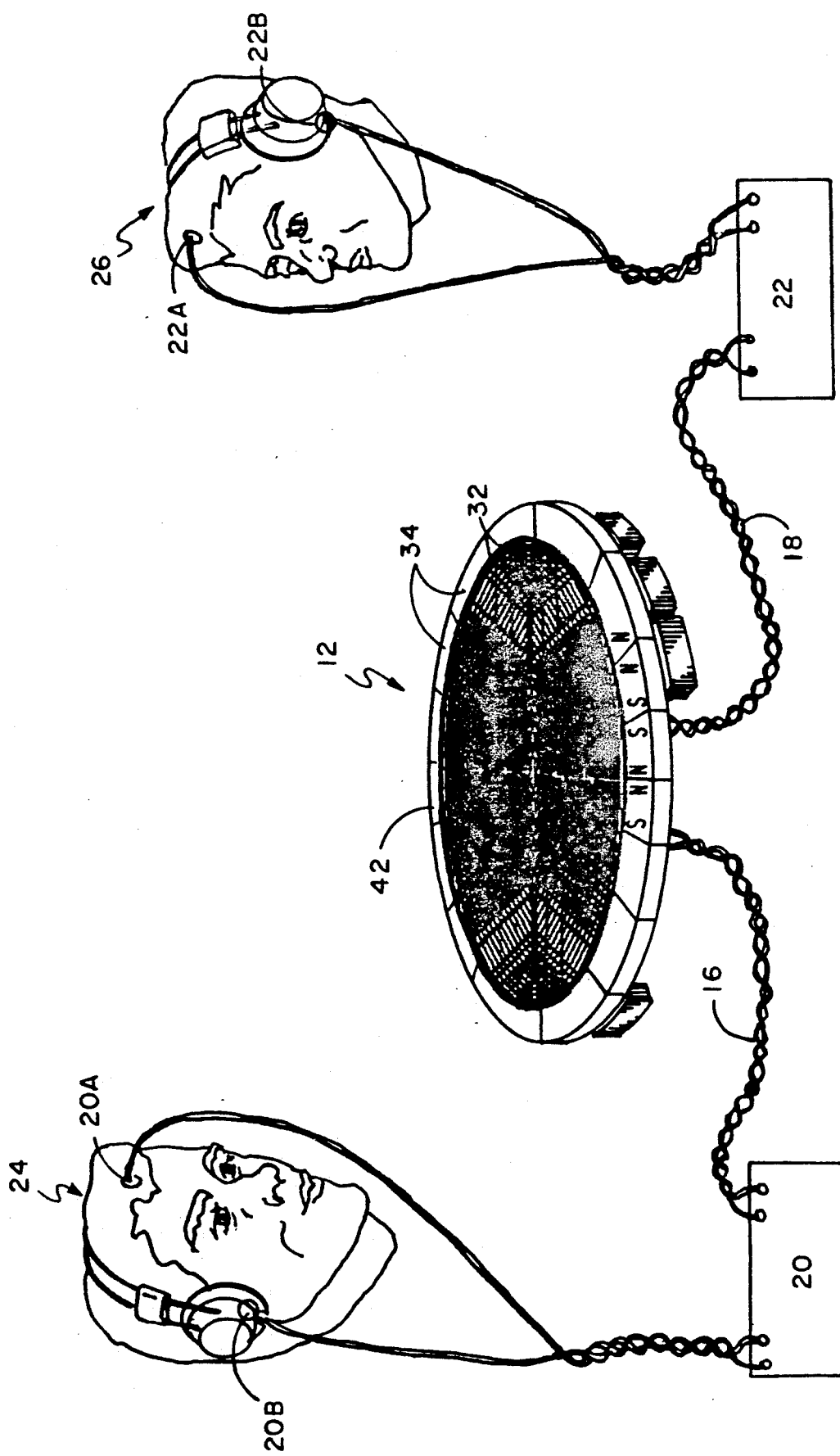
FIG. 2 illustrates a perspective top view of the device of this invention with two players playing connected thereto through headsets.
Figure 4:
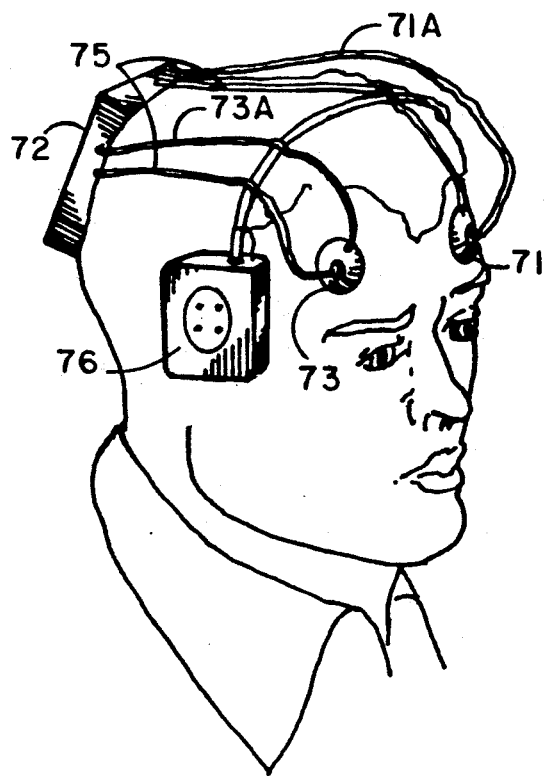
FIG. 4 illustrates an electrode cap.

FIG. 1 illustrates a cross-sectional view through the brain wave-directed amusement device 10 of this invention showing a rotating optical display pattern on its upper surface 12. Brain wave or biofeedback monitor 14, which devices are well known in the art and of which there can be one for each player, has input 16 from the brain wave electrodes of a player such as seen in FIG. 2. Alpha, beta, delta and/or theta wave monitors 20 and 22 are seen separately in FIG. 2 but which can be incorporated into the structure of the device of this invention and are respectively connected to electrodes 20a and 20b and 22a and 22b on the heads of first and second players 24 and 26, the outputs of which feed into brain wave monitors 20 and 22 which then, for each player, measures the intensity of the waves and directs the amount of wave feedback similar to monitor 14 in FIG. 1 to a proportional controller. Monitors 20 and 22 are connected to head-contacting electrodes as more clearly seen in the cap of FIG. 4. In FIG. 4 monitor 72 is connected to electrodes 71 and 73 through the dual wire lead 78. Cap 70, which can also support earphones 76 can have members 71a and 73a help to support electrodes 71 and 73 against the skin. A proportional controller, such as controller 28 in FIG. 1 takes monitor output as numerical information and in proportion thereto directs current to a series of electromagnets 30 beneath rotatable top plate 32 so as to cause top plate 32 which contains permanent magnets 34 therein to start rotating relative to the amount of brain waves produced.

Figure 5:
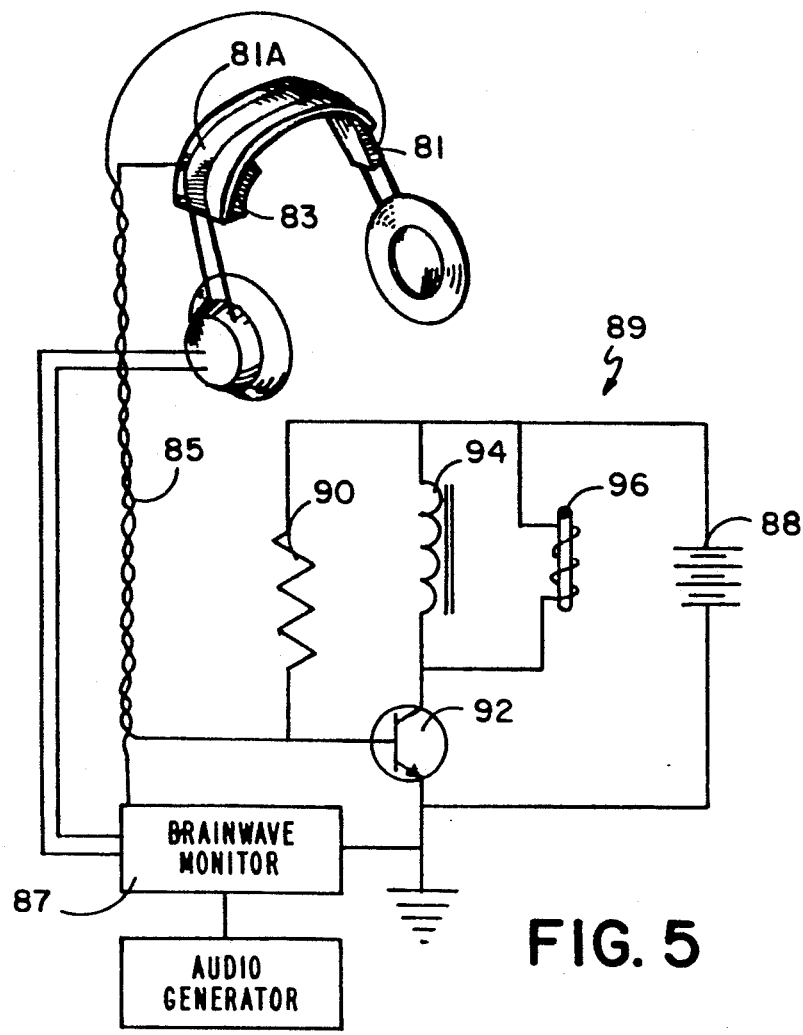
FIG. 5 illustrates an arrangement for a proportional controller.

FIG. 5 illustrates a simple circuit for a proportional control which will vary the power of an electromagnet based on the signal strength from a monitor lead as described further below. Also within some embodiments of the device can be liquid crystal display 36 and crystal display pattern memory unit 40 as seen in FIG. 1. Such LCD displays are well known in the art to produce a variety of design displays. Liquid crystal display 36 is disposed beneath rotating top plate 32 which can be a substantially transparent sheet with a pattern 42 imprinted thereon as seen in FIG. 2. The liquid crystal display pattern can be selected from many stored in the liquid crystal display and pattern memory 40 operated by control knobs 44 by the player(s) to display one of the stored patterns. As the substantially transparent top plate 32 rotates due to on-and-off attraction of electromagnet 30 and repulsion of permanent magnets 34 which movement is controlled by the amount of brain waves produced, a variety of moire patterns such as seen in FIG. 2 will be produced and observed by the player(s). In some embodiments an oil boundary layer between the upper and lower fringe pattern plates can be used. Optical transmitting grade oil works well. In some embodiments the Moire patterns can be printed onto two bi-directionally oriented, biofringent transparent sheets and viewed by back lighting when positioned between light-polarizing transparent sheets or gratings to produce an effective display. When more than one player is connected to the device, there can be a competitive game to see who can rotate the device further in the direction that is controlled by each player with, for example, one player controlling the rotation clockwise and the other player controlling the rotation counterclockwise. As can be seen in FIG. 2, the plurality of fixed magnets 34, each having north and south poles on rotating top plate 32 and electromagnets 30 thereunder can cause the movement of top plate 32 by changing their polarities or by becoming activated or deactivated in a sequence. The device of this invention can include a computer counter to determine how many rotations each player has caused to move in his direction as well as the speed of rotation. Therefore a winner can be determined being the player who has produced the most brain waves.

Figure 3:
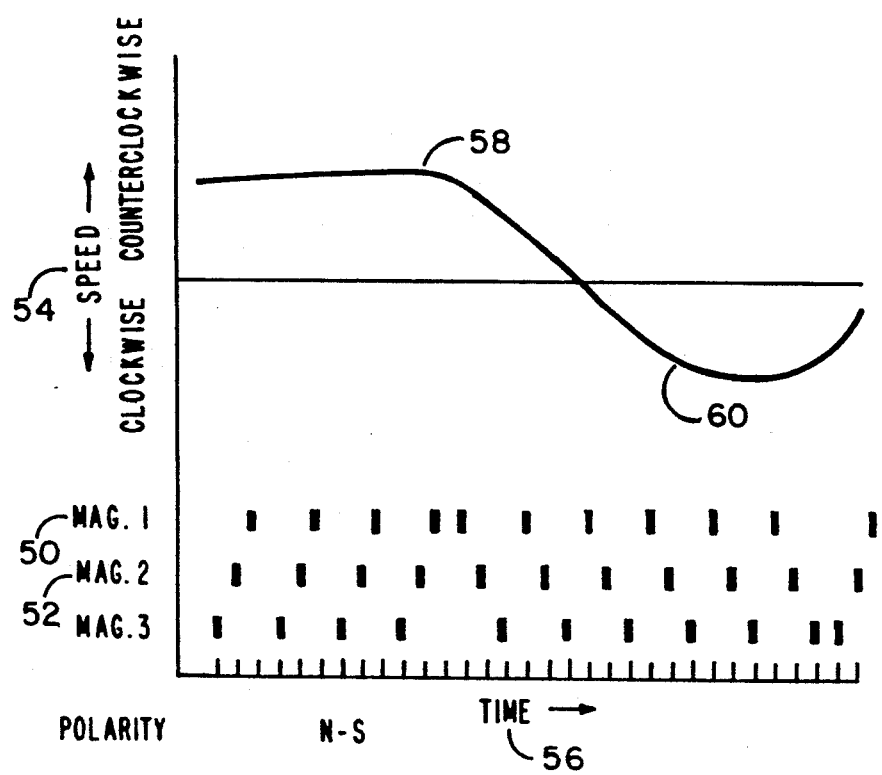
FIG. 3 is a graph of the magnetic activations of the rotating plate over time showing speed and movement clockwise and counterclockwise.

FIG. 3 illustrates a graph showing the series of magnets wherein speed 54 of rotation related to time 56 may be clockwise 60 or counterclockwise 58 depending upon each player's control of the sequence of the activation of the various electromagnets positioned under top plate 32.

FIG. 4 illustrates the embodiment of the system of a cap containing electrodes 71 and 73. From electrodes 71 and 73 in cap 70 extend lines 78 to biofeedback monitor 72 and which can be mounted on cap 70.

Many types of cap monitors on the head can be utilized such as the one illustrated in FIG. 5 where contact electrodes 81 and 83 extend over the crown of the head inside cap 81a and are interconnected by lines 85 to brain wave monitor 87 which monitor directs a portion of the signal from the electrode cap through proportional controller 89 to electromagnet 96, similar to electromagnet 30 in FIG. 1, wherein the amount and sequence of current running to electromagnet 96 will help control the direction of movement and speed of rotation of the upper plate depending upon the ability of the player to create the brain wave signals necessary. Part of brain wave monitor 87 can contain an audio generator for production of music or various tones which music or tones can be altered by the players' changing of brain waves. A portion of the signal is directed through a battery 88 to one portion of the coil around electromagnet 96 while the other portion at the other end of the coil around electromagnet 96 extends from line 85 through transistor 92 by transformer 94 and resistor 90 which will increase or decrease the amount of current passing through electromagnet 96 from battery 88 by increasing or decreasing the power depending upon the signal entering transistor 92 along lines 85.

Figure 6:
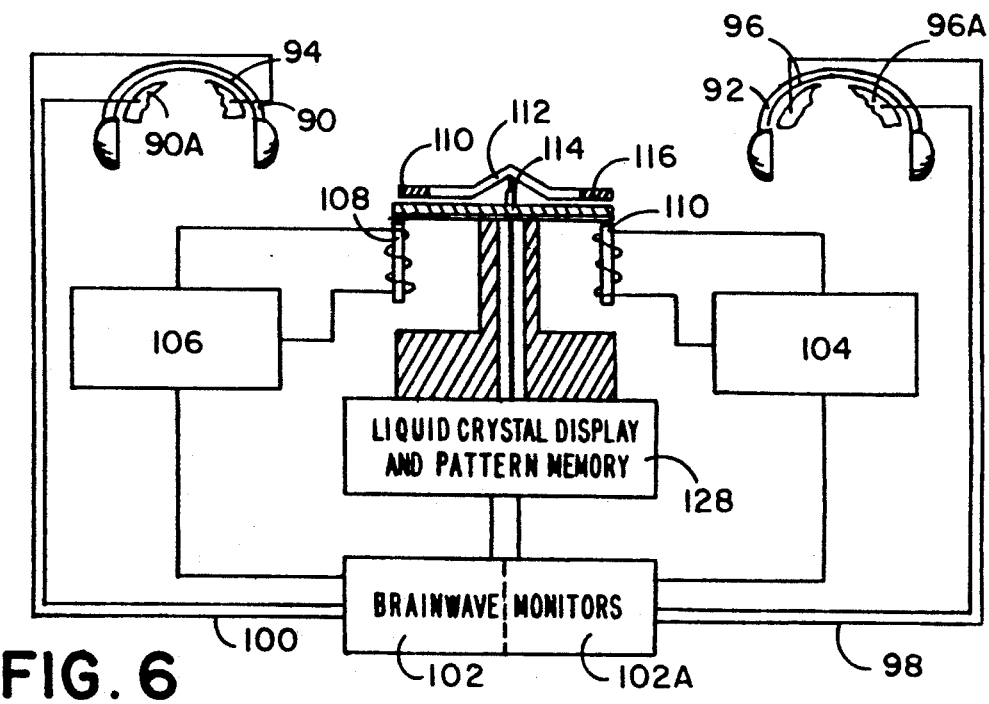
FIG. 6 illustrates a dual cap system for operating a rotating display.

FIG. 6 illustrates a game utilizing circuitry similar to that of FIG. 5 but for two players wherein first and second caps 90 and 92 respectively carry first and second pairs of contact electrodes 94 and 94a and 96 and 96a with a signal being directed respectively along first and second dual lines 100 and 98 to dual brain wave monitors 102 and 102a, each of which then directs a portion of its signal through first and second boxes 104 and 106 including amplifier circuits sequenced to direct electromagnets 108 and 110. First and second electromagnets 108 and 110, depending upon the intensity of the electromagnetic field, will drive rotating top plate 112 on pin shaft 114 which provides low resistance to rotational movement. There is a plurality of magnets such as magnets 116 and 118 located in the outer periphery of rotating upper top plate 112 each of which is activated in sequence as described below. The brain wave monitor can also drive the signals to liquid crystal display pattern memory 128 which will display a pattern under rotating top plate 112. In this way the device of this invention can be competitively used by two players.

Figure 7:
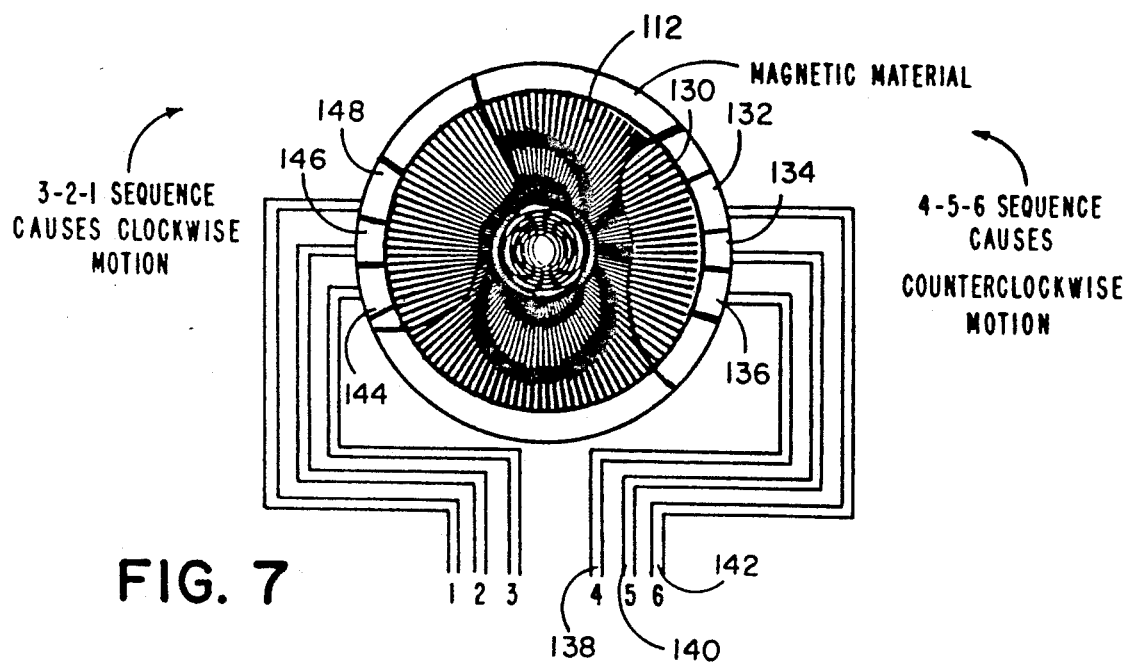
FIG. 7 illustrates a top view of the rotating top plate of this invention.
Figure 8:
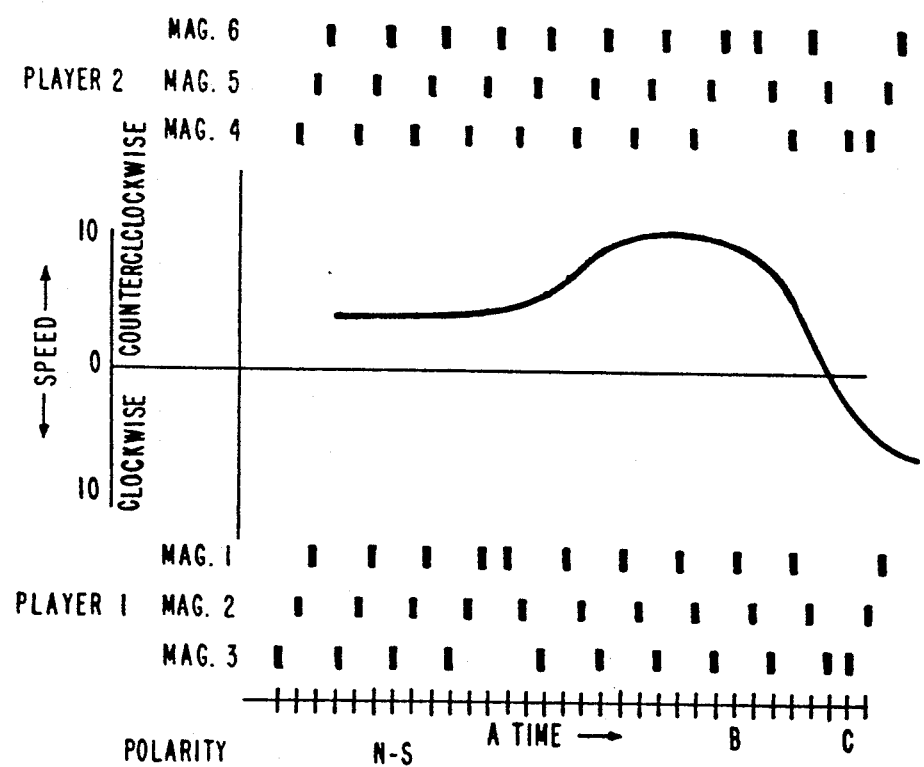
FIG. 8 illustrates a graph of the magnetic activations of two players over time showing speed and movement clockwise and counterclockwise of the rotating top plate.

FIG. 7 is a top view of the display unit of this device showing portions of top plate 112 cut away, exposing lower plate 130 which has a plurality of discrete electromagnets such as, for example, electromagnets 132, 134 and 136 of one player and electromagnets 144, 146 and 148 for the other player disposed around its outer periphery, such electromagnets being interconnected by pairs of wires from the windings such as wire pair 138 which extends to magnet 136, wire pair 140 extending to magnet 134, and wire pair 142 extending to magnet 132. Opposite player magnets can be seen on the other side of the plate so that in a sequence of activations, for example, magnets 144, 146 and 148 being activated in the listed sequence will cause a clockwise rotation of upper plate 112 which has magnets or magnetically attractive material in its periphery whereas an activation in sequence of magnets 132, 134 and 136 will cause a counterclockwise motion. Each group of magnets can be controlled by a different player with magnets 144, 146 and 148 controlled by a first player and magnets 132, 134 and 136 being controlled by the second player. The magnets can be arranged, as depicted in the graph in FIG. 8 wherein magnet activation is shown in dashes relevant to magnets 1, 2 and 3 belonging to Player 1 and magnets 4, 5 and 6 belonging to player 2. Counterclockwise movement is shown above the axis and clockwise movement below the axis with speed of rotation being indicated by the frequency of the magnetic activations wherein one can see from the graph that movement was first counterclockwise increasing in speed and then slowing to a gradual movement clockwise as player 1 takes over control of the rotating plate. In this way the play can continue with each player attempting to gain dominance through brain wave production.

Figure 9:
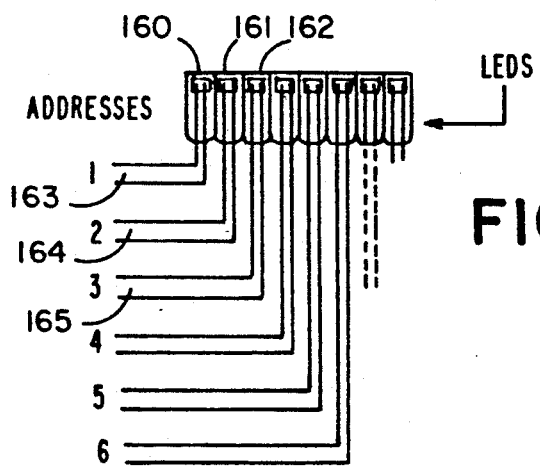
FIG. 9 illustrates a cross-sectional side view of a section of the lower plate showing an arrangement of LEDs.
Figure 10:
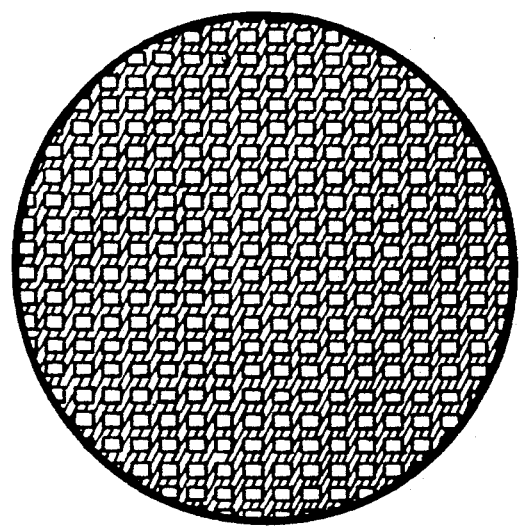
FIG. 10 illustrates a top view of the lower plate showing an arrangement of LEDs against a dark background.
Figure 11:
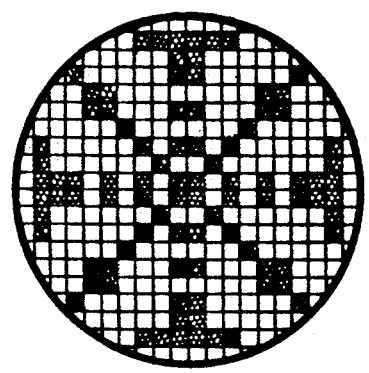
FIG. 11 illustrates the lower plate of FIG. 10 with certain of said LEDs illuminated.
Figure 12:
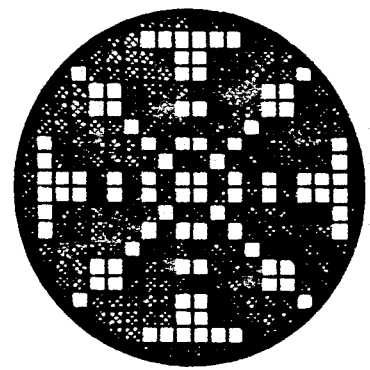
FIG. 12 illustrates the lower plate of FIG. 11 with the remaining LEDs illuminated and with the initially illuminated LEDs not illuminated.
Figure 13:
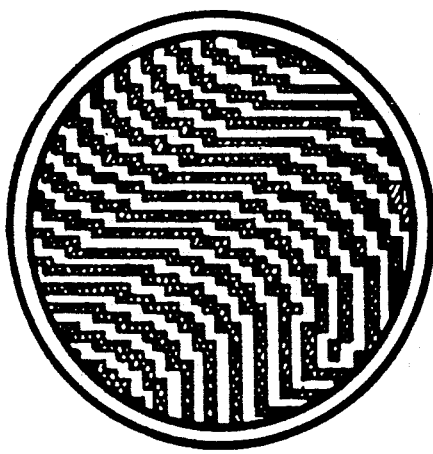
FIG. 13 illustrates a lower plate having a liquid crystal pattern thereon.

FIG. 9 illustrates a cross-sectional side view of the bottom plate showing an arrangement of separately controlled LEDs such as 160, 161, 162 and so on, each being activated through a pair of wires such as wire pairs 163, 164 and 165. By individually activating these wires as controlled by the display pattern memory unit, one can produce a variety of lower plate patterns as seen in FIG. 11 or as in a similar pattern with the LEDs activated and unactivated being opposite in FIG. 12. FIG. 10 illustrates a top view of an array of LEDs of the bottom plate which can be activated as seen in FIGS. 11 and 12 in a variety of configurations with each LED either on or off and with either a light or dark background around the LEDs. Also a fringe pattern such as seen in FIG. 13 can be produced when using a black field liquid crystal display sheet. The display configuration selection could be made by the players of the game.

Figure 14:
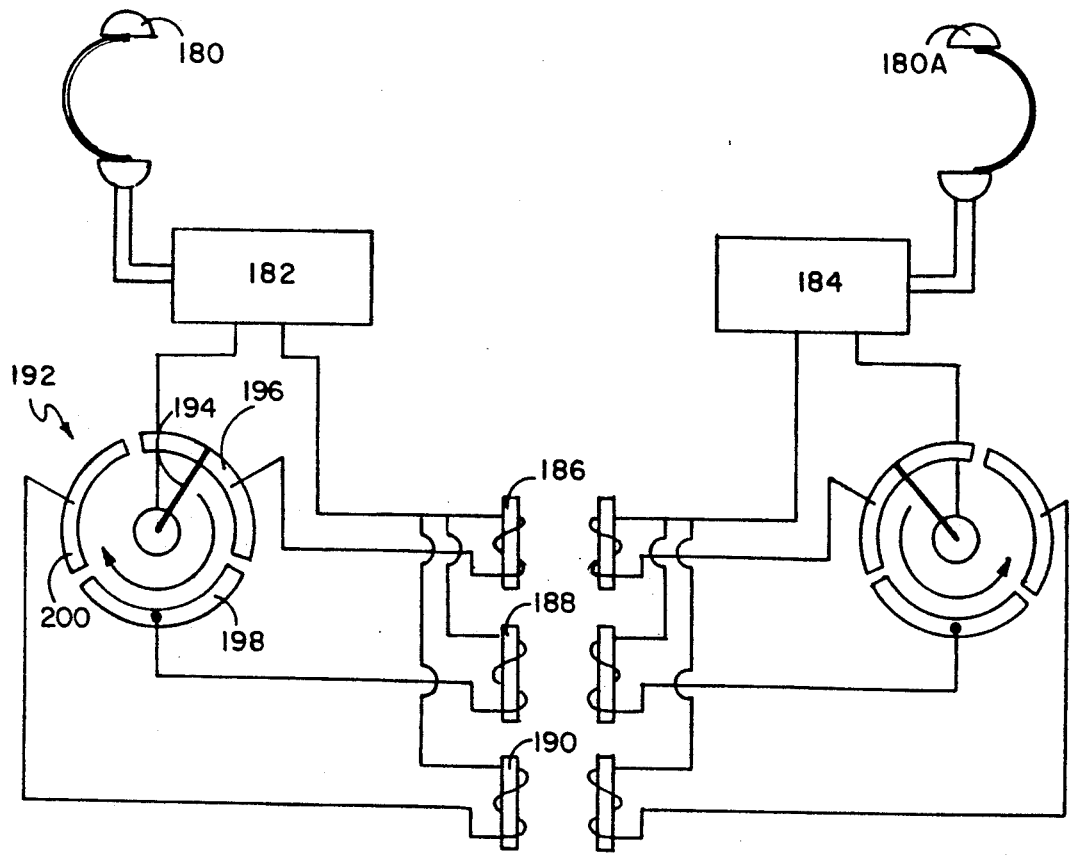
FIG. 14 illustrates circuitry for the activation of individual electromagnets in the lower plate.

FIG. 14 illustrates how control of each of a plurality of magnets can be sequenced from magnet to magnet over a period of time with brain wave electrode cap 180 and 180a sending signals through motor and current distribution circuitry 182 and 184 to the various electromagnets illustrated as 186, 188 and 190 where each electromagnet is interconnected into the circuit by distributor 192 which has a rotating contact member 194, rotated by a motor with adjustable speed, such contact member 194 rotating over contacts 196, 198 and 200 which are interconnected respectively to electromagnets 186, 188 and 190. By rotating the speed of contact member 194 of distributor 192, magnets 186, 188 and 190 will be alternately powered in a series as the distributor rotates over the contact members with insulative spaces between the contact members so that when, for example, as seen in FIG. 14 contact member 194 is resting on contact 196, only magnet 186 will receive the current and be empowered. When rotating member 194 rotates onto the next contact 198, magnet 188 will be activated and so on. The speed of the rotation of the distributor to the various magnets will cycle through the magnets, and the power in each will determine how fast the top plate will rotate.

Figure 15:
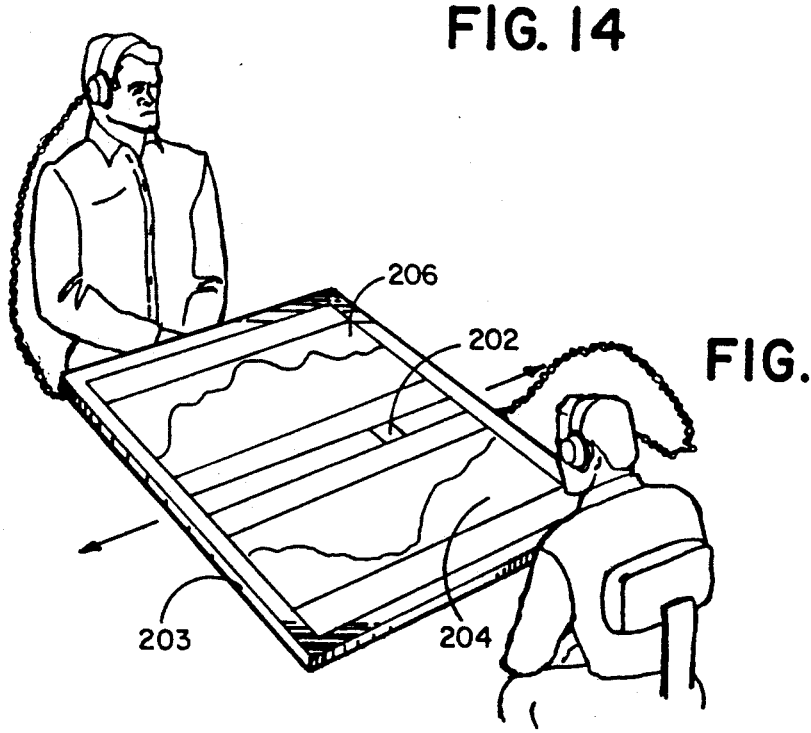
FIG. 15 illustrates an alternate embodiment of the device where players strive to move an illuminated spot from one side of the game board to the other side.

Another embodiment of a biofeedback game as seen in FIG. 15 uses a box 203 with an illuminated square 202 in the center of a viewing board and a digital display which acts as an indicator of the summation of total brain waves produced. A variety of illuminated squares can be illuminated in sequence by, for example, having each square illuminated only at a particular brainwave intensity with the activation intensity increasing from one end of the display to the other so that the illuminated square would appear to move as the brainwaves intesity increased and the adjacent squares sequentially became illuminated. When a player has managed to move his illuminated square all the way to his side of the board first, that player wins. The board also can include two digital displays 204 and 206, each of which shows a graph of each player's brain wave intensity such as an EEG readout which display can be of the type which produces a graph continuously at the right side of the screen as the older part of the graph disappears on the left side of the screen.

Figure 18:
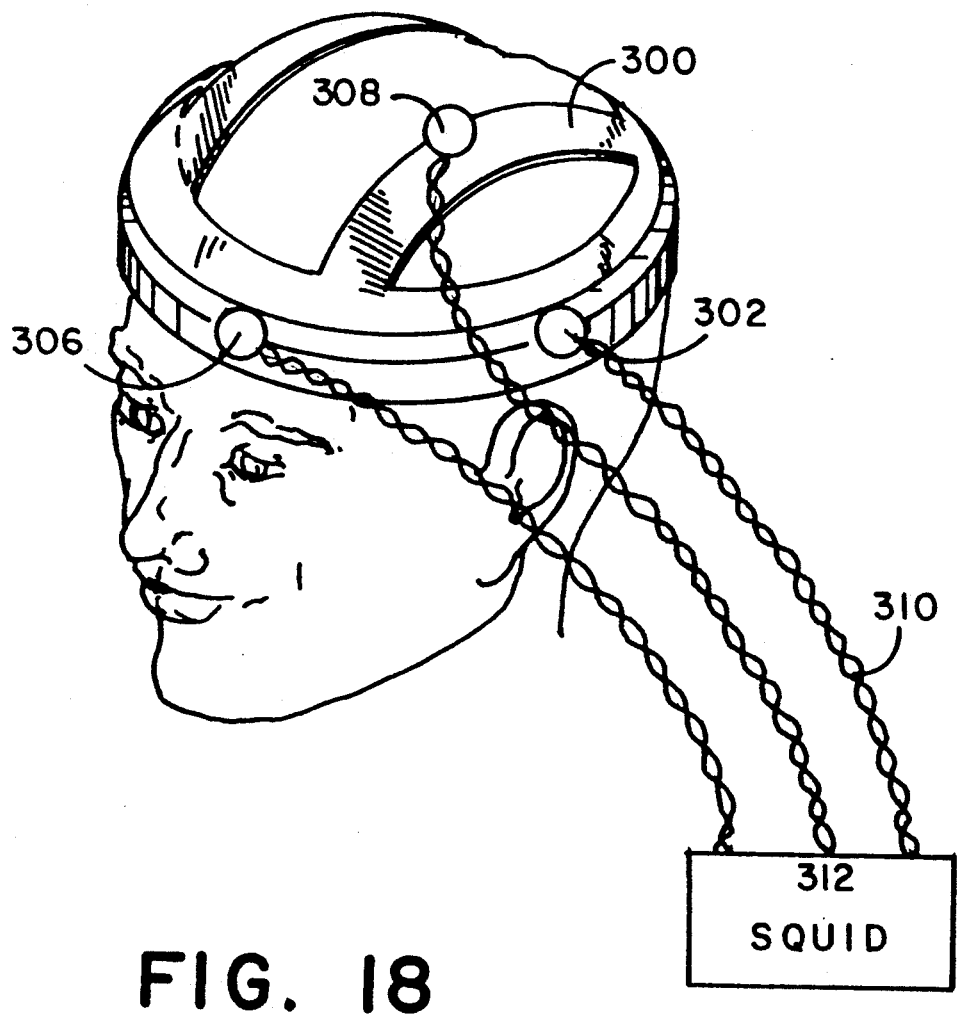
FIG. 18 illustrates a cap employing a superconducting quantum interference device to detect brainwaves.

In another embodiment of this invention seen in FIG. 18 the brain waves of the players can be detected and measured by a magnetic coil and by a super-conducting quantum interference device called a SQUID, which type of device is well-known. A SQUID device combines magnetic flux quantization and Josephson tunneling and can detect and measure very weak magnetic fields. Whereas the embodiments previously described detect the brain waves by sensing and measuring voltages picked up by electrodes that are in contact with the player's head, a SQUID device which is not in contact with the head detects and measures brain waves by detecting and measuring magnetic field variations that are outside the head using magnetic pickup coils. The detection and measurement of the magnetic fields produced by brain activity is called magnetoencephalography or MEG. A small single turn or multiturn magnetic pickup coil 1-3 cm in diameter such as coil 302 can be placed near the head on the side or front, or back of the head, or above the head; and the two ends of the coil are connected to the player's SQUID via a pair of twisted wire leads 310 that can be shielded to guard against electronic pickup noise.

The coil(s), such as coils 302, 306 and 308 can be mounted on a comfortable headpiece 300, made of a material, such as plastic, that is non-magnetic and electrically non-conducting. The SQUID device 312 itself, which operates at low temperatures such as 77 degrees Kelvin, can be placed at a convenient location such as on a table several feet away from the player. The output leads from each player's SQUID are connected to the rest of the game equipment in the same way as the outputs from the brain wave monitors in the previous embodiments.

The signals from the brain wave cap and monitor can further be transformed to create movement of the top plate if one uses a reversible DC motor. As seen in FIG. 16, one can pick up from cap electrode 230 a signal and direct it through a series of op amps which can be a Radio Shack No. 2761715 or equivalent such as first op amp 232 which directs to a second op amp 234 and a third op amp 236 which respectively keeps increasing the signal strength where it can then be passed through a rectifier 238 which can be a Radio Shack 2761151 or equivalent which produces a positive DC voltage. The DC voltage is then amplified again through a fourth operational amplifier 240 through a variable resistor 242 to control the output of each player should any circuit adjustment be necessary. The DC motor 244 then receives one player's input at its positive input 246 and the second player's input at its negative input 248. The higher the differential, the greater the movement with the direction of movement being changeable due to the polarity of the input signals to the motor. Each player produces a positive voltage output at the motor. If one produces a greater positive voltage, then the motor will turn in the direction of that player's electrical contact with the motor. The greater the difference in DC potential from one player to another, the more the motor rotates. The game can also be driven by battery power which is regulated by the brain wave production control circuitry as discussed above or can even have an AC power input.

AC current can also be directed to a power supply transformer which can charge batteries to operate the device of this invention. A basic circuit, as seen in FIG. 17, shows the output of the electrode caps such as cap 250 put through a low-noise amplifier 252 which passes to a frequency modulator 254 to a buffer amplifier 256 to an audio amplifier 258, and then the amplified signal is directed to an operational amplifier 260 which has a comparative circuit 262 and a high gain amplifier 264 which directs the signal to DC motor 268 which rotates in the direction as controlled by the player with the highest voltage potential coming from his electrode cap.

The game of this invention can also be used in the health field for patients who suffer from attention disorders. As the device is amusing, concentration time can be lengthened during play, making the device useful in therapy. The use of the device would further reveal information about or help in the therapy of people, especially children suffering from autism and/or hyperactivity and with sensory input and concentration problems. Since an autistic person often creates commotion in his environment to keep his sensory input high, such input will be occupied by my invention during concentration and there will be a therapeutic and training effect. Autistic children are frequently more interested in objects than they are in people, and so it is natural that the autistic child would be interested in the device of this invention. Further, there may be uses involving the negative response when a autistic child would have a bad experience with such a device, it may prove that the child would prefer the attention of people rather than objects for a period after such a response. When the trainee is outputting the proper brain activity, the device responds by maintaining the sensory input which reinforces the activity. Alternatively, the device could respond by rewarding the trainee with a sensory response and then default to a work-producing mode so that the trainee would have to self-motivate to obtain a reward again.

Although the present invention has been described with reference to particular embodiments, it will be apparent to those skilled in the art that variations and modifications can be substituted therefor without departing from the principles and spirit of the invention.

I claim:

1. A game comprising:
   means for detecting brainwave intensity of a player;
   means for the conversion of brainwave intensity detected by said detection means to electrical impulses, the intensity of said electrical impulses being proportional to the intensity of said brainwave;
   a rotatable circular member having a changing visual display thereon, the changing of said visual display being dependent on the speed of rotation of said rotating circular member; and
   means for rotating said circular member with the speed of said rotation being proportional to the intensity of said electrical impulses.

2. The game of claim 1 wherein brainwave intensities are detected from at least two players and said display is activated in proportion to the intensity of said electrical impulses converted from the player producing the more intense brainwaves.

3. The device of claim 2 wherein said means for detecting brain waves includes a brain wave monitor contained on a cap worn on the head of each player.

4. The device of claim 2 wherein an audio generator generates tones, which can be in the form of music, into earphones worn by each player for that player to have changes in brain waves which generate, because of their changes in intensity, various patterns on said visual display.

5. The device of claim 2 with each player having means to interrupt another player's brain wave input to disrupt that player's brain wave intensity.

6. The game of claim 2 wherein the rotation in one direction of said rotating circular member having a visual display thereon is controlled by the intensity of the electrical impulses of one player and the rotation in the other direction is controlled by the intensity of electrical impulses of the other player with the more intense electrical impulses moving the display in the direction of rotation controlled by the player producing the more intense brainwaves.

* * * * *